United States Patent
Herleikson

(10) Patent No.: US 6,625,487 B2
(45) Date of Patent: Sep. 23, 2003

(54) BIOELECTRICAL IMPEDANCE ECG MEASUREMENT AND DEFIBRILLATOR IMPLEMENTING SAME

(75) Inventor: Earl C. Herleikson, Lebanon, ME (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/908,293

(22) Filed: Jul. 17, 2001

(65) Prior Publication Data

US 2003/0032989 A1 Feb. 13, 2003

(51) Int. Cl.[7] .............................................. A61N 1/39
(52) U.S. Cl. ............................. 607/8; 600/547; 607/28
(58) Field of Search ..................... 607/8, 28; 600/547

(56) References Cited

U.S. PATENT DOCUMENTS

| | | | |
|---|---|---|---|
| 4,141,351 A | 2/1979 | James et al. | 126/2.06 |
| 4,263,920 A | 4/1981 | Tasto et al. | 128/734 |
| 4,291,699 A | 9/1981 | Geddes et al. | 178/419 |
| 4,355,646 A | 10/1982 | Kallok et al. | 128/786 |
| 4,617,939 A | 10/1986 | Brown et al. | 128/734 |
| 4,721,110 A | 1/1988 | Lampadius | 128/419 |
| 4,733,667 A | 3/1988 | Olive et al. | 128/419 |
| 4,884,576 A | 12/1989 | Alt | 128/419 |
| 5,201,865 A | 4/1993 | Kuehn | 128/419 |
| 5,501,230 A | 3/1996 | Laribiere | 128/696 |
| 5,685,316 A | 11/1997 | Schookin et al. | 128/713 |
| 5,749,369 A | 5/1998 | Rabinovich et al. | 128/734 |
| 5,791,349 A | 8/1998 | Shmulewitz | 128/734 |
| 5,824,029 A | 10/1998 | Weijand et al. | 607/122 |
| 6,208,898 B1 * | 3/2001 | Gliner et al. | 607/8 |
| 6,278,894 B1 * | 8/2001 | Salo et al. | 600/547 |
| 6,393,317 B1 * | 5/2002 | Fukuda et al. | 600/547 |

* cited by examiner

Primary Examiner—George R. Evanisko

(57) ABSTRACT

A multivariate impedance (Z) measurement module, for use in an electrotherapy device, that accurately measures patient impedance. The Z measurement module implements a resistive network model of the patient's body defined by one or more equations each including resistive elements that represent the impedance of a current paths through the patient. The Z measurement module utilizes at least three electrodes placed at predetermined relative locations on the patient's body, and measures the voltage across different electrode pairs while an applying an alternating current through certain electrodes. The applied current and measured voltages are used to solve the patient model equations for the individual resistive elements. Thus, each individual impedance component is separately and accurately determined.

10 Claims, 5 Drawing Sheets

BIOELECTRICAL IMPEDANCE ECG MEASUREMENT AND DEFIBRILLATOR IMPLEMENTING SAME

BACKGROUND OF THE INVENTION

1. Field of the Invention

The present invention relates generally to electrotherapy devices and, more particularly, to measuring patient impedance in an electrotherapy device.

2. Related Art

Electrotherapy devices are used to provide electrical shocks to treat patients for a variety of heart arrhythmias. For example, external defibrillators typically provide high-energy shocks to a patient, usually through a pair of electrodes attached to the patient's torso. External defibrillators are used to convert ventricular fibrillation or shockable tachycardia to a normal sinus rhythm. Similarly, external and internal cardioverters can be used to provide shocks to convert atrial fibrillation to a more normal heart rhythm.

Conventional external defibrillators have been used primarily in hospitals and other medical care facilities. While these external defibrillators have been known for years, they have generally been large and expensive making them unsuitable for use outside of a medical care facility. More recently, portable external defibrillators for use by first responders have been developed. Portable defibrillators allow medical care to be provided to a patient at the patient's location considerably earlier than preceding defibrillators, increasing the likelihood of survival.

With recent advances in technology, portable defibrillators have become more automated, allowing even a minimally trained operator to use such devices to aid a heart attack victim in the critical first few minutes subsequent to the onset of sudden cardiac arrest. Such portable defibrillators, referred to as automatic or semi-automatic external defibrillators (generally, AEDs), may be stored in an accessible location at a business, home, aircraft or the like.

Generally, manual external defibrillators are configured by an operator for the particular patient and patient condition. In contrast, such determinations are made by the AED for the patient. One of the configuration parameters that needs to be determined is before administering a defibrillating pulse is the energy to be delivered by that pulse. Most AEDs use a fixed energy level. Many of today's AEDs make some level of adjustment of the defibrillation waveform to compensate for different levels of patient impedance. Typically, conventional approaches for measuring patient impedance in electrotherapy devices involve driving the electrodes with a high impedance current source at a frequency greater than 500 Hz and measuring the voltage across the electrodes at the frequency of the current source. From this, the impedance of the current path that includes the two electrodes is determined.

Such an impedance measurement may provide useful information for certain purposes such as to estimate the impedance of the entire defibrillator path, heart rate, respiratory rate and other physiological parameters. However, such an approach fails to provide the information necessary to make an accurate estimation of patient size. For example, it is not uncommon for the impedance value measured using such traditional techniques to be approximately the same for a large adult male and a pediatric patient. Furthermore, the impedance measured in a two-electrode system will increase due to poor electrode contact interfering with the accurate determination of actual body impedance. It follows, then, that such measured values are insufficient to differentiate between patients of different body mass and to determine the optimal defibrillating current to be applied to a given patient.

SUMMARY OF THE INVENTION

The present invention is directed to an electrotherapy device with an improved apparatus and methodology for accurately measuring patient impedance. The invention implements a resistive network model of the patient's body that includes one or more equations including resistive elements each representing the impedance components of the current paths through the patient. The present invention utilizes at least three electrodes placed at predetermined relative locations on the patient's body, and measures the voltage across different electrode pairs while an applying an alternating current through certain electrodes. The applied current and measured voltages are used to solve the patient model equations for the individual resistive elements. Thus, each individual impedance component is separately and accurately determined.

There are numerous benefits provided by the determination of patient impedance separate from the other impedance values in the current flow path(s). In contrast to conventional approaches in which a single impedance value is determined for all current flow paths through the patient, the patient impedance generated in accordance with the present invention is not lumped or combined with other impedance values such as electrode-to-skin impedance. As a result, the patient impedance determined by the present invention is more accurate and, therefore, can be used to accurately determine patient size and the optimal energy to be delivered with an applied pulse. Similarly, the impedance values determined in accordance with the present invention can also be utilized to increase the accuracy of other determinations such as respiratory rate, cardiac output, proper electrode placement, effects of CPR and the like.

A number of aspects of the invention are summarized below, along with different embodiments that may be implemented for each of the summarized aspects. It should be understood that the summarized embodiments are not necessarily inclusive or exclusive of each other and may be combined in any manner in connection with the same or different aspects that is non-conflicting and otherwise possible. These disclosed aspects of the invention, which are directed primarily to systems, methods, data and techniques related to measuring bioelectrical impedance, are exemplary aspects only and are also to be considered non-limiting.

In one aspect of the invention, a multivariate impedance measurement module for use in an electrotherapy device such as a cardioverter, a defibrillator and a pacemaker is disclosed. The multivariate impedance measurement module implements a resistive network model of a patient's body that is defined by voltage/current equations having terms representing an impedance of current paths between electrodes through the patient. In one embodiment, the measurement module utilizes at least three electrodes placed at predetermined relative locations on the patient's body. The module successively measures a voltage across different pairs of the electrodes while applying an alternating current through a selected pair of electrodes.

The resistive network patient model includes resistive elements each representing an impedance of a current path that connects nodes of the network model. The nodes include the electrodes.

The resistance elements can include a plurality of resistive elements each representing an electrode/skin impedance between each of the at least three electrodes and a corresponding location at which current delivered by each the electrode is delivered into the patient's body. The resistance elements can also or alternatively include an impedance of each current path from a location at which current is delivered into the patient's body and a geometric center of the patient model and an impedance of a current path from a first location at which current is delivered into the patient's body to a second location at which current exists the patient's body.

In another aspect of the invention, an electrotherapy device for applying a therapeutic shock to a patient such as a cardioverter, a defibrillator and a pacemaker is disclosed. The module includes at least three electrodes for placement in a predetermined relative position on the patient's body; and a multivariate impedance measurement module that applies an alternating current through one or more electrode pairs while concurrently measuring a voltage across successive electrode pairs.

The electrodes are placed at predetermined relative locations on the patient's body such that a geometric center of the electrodes is approximately located at the patient's heart. The module implements a resistive network model of the patient that includes resistive elements each representing an impedance of a current path between nodes of the network model. The patient model is defined by a plurality of voltage and/or current equations each including terms representing the impedance of the current paths. The module utilizes the applied current and measured voltages to solve the plurality of resistive network patient model equations for the unknown impedance terms.

The resistive elements can include, for example, a plurality of resistive elements each representing an electrode/skin impedance between each electrode and a corresponding location at which current delivered by that electrode is delivered into the patient's body; an impedance of each current path from a location at which current is delivered into the patient's body and the geometric center of the patient model or an impedance of a current path from a first location at which current is delivered into the patient's body to a second location at which current exists the patient's body.

In a still further aspect of the invention, a method for measuring patient impedance is disclosed. The method includes (1) applying at least three electrodes to a patient's body at predetermined relative locations such that a geometric center of the electrodes is located approximately at the location of the natural heart; and (2) applying an alternating current to a first pair of electrodes. In addition, the method includes (3) successively measuring voltage across a plurality of pairs of electrodes during the application of the alternating current; and (4) solving a resistive network model defined by a voltage and current equations each expressed in terms of unknown resistance values each representing an impedance component along a current path through the patient from one electrode to another electrode of the first electrode pair.

Various embodiments of the present invention provide certain advantages and overcome certain drawbacks of conventional impedance measurement techniques. Not all embodiments of the invention share the same advantages and those that do may not share them under all circumstances. This being said, the present invention provides numerous advantages including the advantages noted above. These and other features and advantages of the present invention as well as the structure and operation of various embodiments of the present invention are described in detail below with reference to the accompanying drawings.

BRIEF DESCRIPTION OF THE DRAWINGS

The above and further advantages of the invention will be more clearly appreciated from the following detailed description when taken in conjunction with the accompanying drawings, in which like reference nunerals indicate like structures or method steps, in which the left-most one or two numerals of a reference numeral indicate the number of the figure in which the referenced element first appears, and in which.

DETAILED DESCRIPTION

I. Introduction and Exemplary Electrotherapy Device Application

Figure 1:
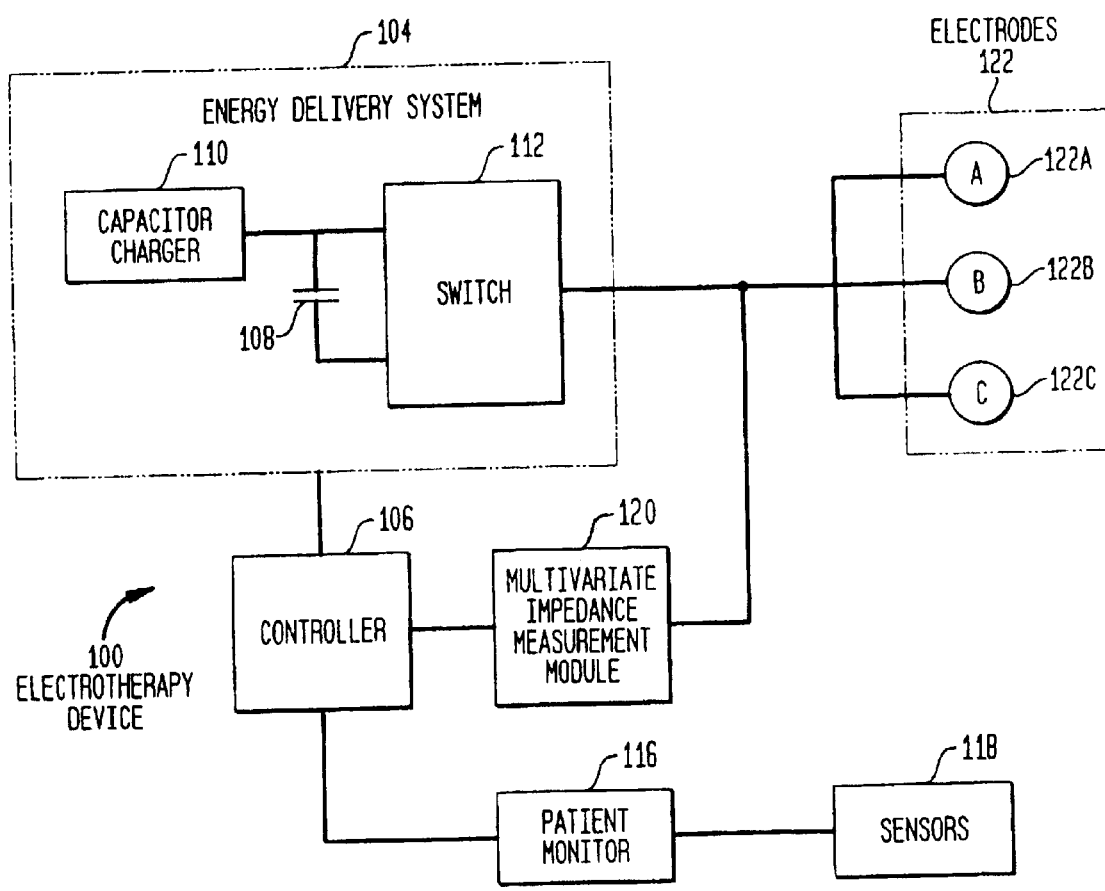
FIG. 1 is a simplified block diagram of an exemplary electrotherapy device implementing a multivariate impedance measurement module in accordance with one embodiment of the present invention.

The present invention is directed to an electrotherapy device with an improved apparatus and methodology for measuring the impedance of a patient that isolates and, therefore, accurately determines the impedance of the path to be taken by a therapeutic current through the patient. Aspects and embodiments of the present invention will be described herein with reference to an exemplary electrotherapy device, a simplified block diagram of which illustrated in FIG. 1. Electrotherapy device 100 may include the necessary components to cardiovert, defibrillate or pace a patient, or to perform any combination of such operations. It should be appreciated that since such electrotherapy devices are well known in the art, the components described herein and illustrated in FIG. 1 are exemplary only. In the following description it is envisioned that electrotherapy device 100 is a portable defibrillator such as the many models of portable AED available from Agilent Technologies, Palo Alto, Calif.

Components of electrotherapy device 100 operate under the control of a controller 106. Controller 106 may be embodied in a microprocessor, gate array, ASIC, or other control logic architecture, as well as any combination thereof. Preferably, controller 106 is implemented in software code that is executed on a commercially available microprocessor. Generally, such software code is stored in a memory device (not shown) accessible by the microprocessor.

Electrotherapy device 100 includes an energy delivery system 104 that delivers energy to a patient (not shown). Energy delivery system 104 is connected to three electrodes 122A–C and includes generally a capacitor or capacitor bank 108, a capacitor charger 110 and a switching mechanism 112. In response to controller 106, energy delivery system 104 delivers an electric shock from capacitor 108 to electrodes 122 that are placed in various predetermined locations on the patient.

Patient monitor 116 monitors the patient's heart rhythm and determines whether the monitored rhythm is shockable. Patient monitor 116 receives information from sensors 118, and may be integrated in electrodes 122, as physically separate devices or a combination thereof. Patient monitor 116 communicates a shock decision to controller 106. Energy delivery system 104 then delivers a therapeutic energy pulse to the patient via electrodes 122.

These and other components of electrotherapy device 100 are well known in the art. Electrotherapy devices suitable for implementing the present invention may include the same or similar device components now or later developed. The above and other device components not specifically described in this application may be included and configured to operate in the manner described in U.S. Pat. No. 5,607,454 to Cameron et al., entitled "Electrotherapy Method and Apparatus," the disclosure of which is incorporated herein by reference herein in its entirety.

In accordance with the exemplary aspects of the present invention, device 100 includes a multivariate impedance (Z) measurement module 120 for accurately measuring patient impedance. Multivariate impedance measurement module 120 implements a resistive network model of the patient's body that includes one or more equations including resistive elements each representing the impedance components of the current paths through the patient. Multivariate impedance measurement module 120 utilizes at least three electrodes placed at predetermined relative locations on the patient's body, and measures the voltage across different electrode pairs while an applying an alternating current through certain electrodes. The applied current and measured voltages are used to solve the patient model equations for the individual resistive elements. Thus, each individual impedance component is separately and accurately determined.

There are numerous benefits provided by the determination of patient impedance separate from the other impedance values in the current flow path(s). In contrast to conventional approaches in which a single impedance value is determined for all current flow paths through the patient, the patient impedance generated by multivariate impedance measurement module 120 is not lumped or combined with other impedance values such as electrode-to-skin impedance. As a result, the patient impedance determined by the present invention is more accurate and, therefore, can be used to accurately determine patient size and the optimal energy to be delivered with an applied pulse. Similarly, the impedance values determined in accordance with the present invention can also be utilized to increase the accuracy of other determinations such as respiratory rate, cardiac output, proper electrode placement, effects of CPR and the like.

As should be apparent to those of ordinary skill in the art, multivariate impedance measurement module 120 may be implemented in any well-known manner now or later developed. For example, multivariate impedance measurement module 120 may be implemented as a separate, processor-based system, in hardware circuitry, ASICs, gate arrays and the like. In addition, multivariate impedance measurement module 120 may also include components located within other electrotherapy device subsystems, such as within controller 106.

II. Multivariate Impedance Measurement Module

Figure 2:
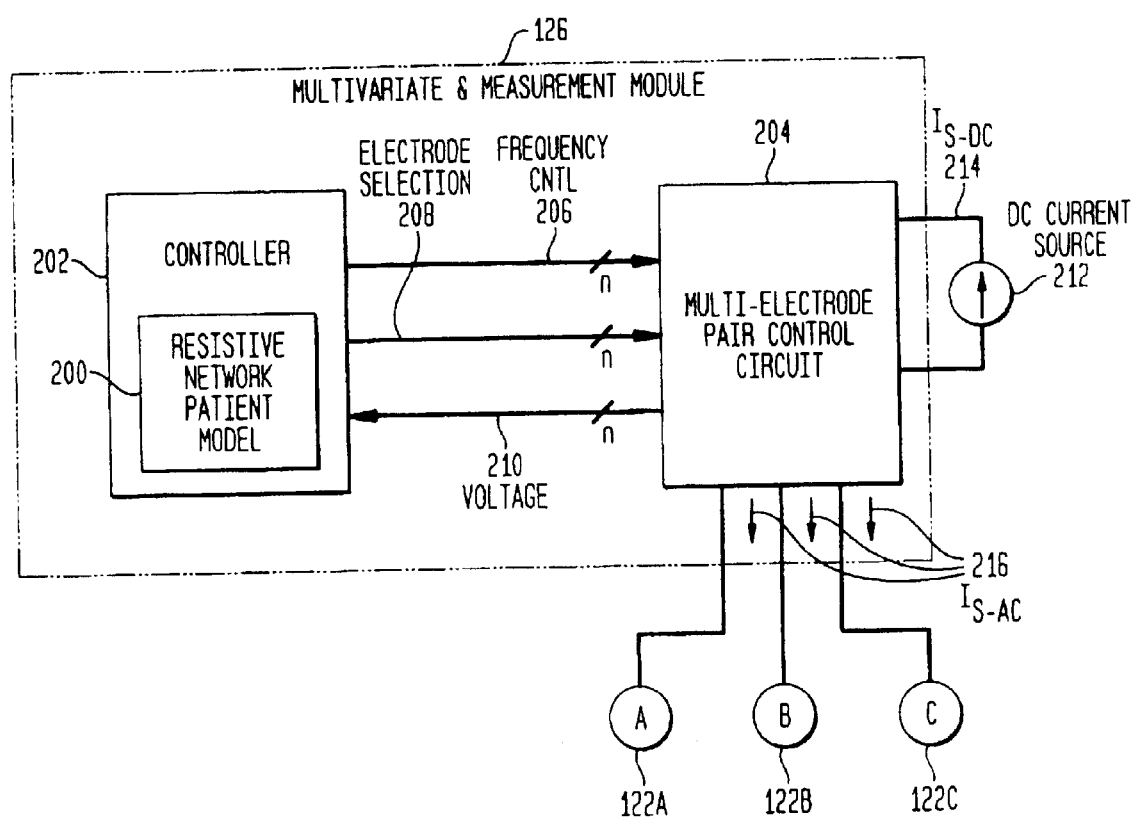
FIG. 2 is a high-level block diagram of one embodiment of the multivariate impedance measurement module of the present invention.

FIG. 2 is a high-level block diagram of one embodiment of the multivariate impedance measurement module 120 of the present invention. Module 120 includes generally a controller 202 and a multi-electrode pair control circuit 204. Multi-electrode pair control circuit 204 is connected to electrodes 122A–122C and DC current source 212. A controller 202 controls multiple electrode pair control circuit 204 as described in detail below to apply an alternating current 216 to, and to obtain voltage measurements across successive pairs of electrodes 122. Controller 202 utilizes the applied currents and measured voltages to solve an implemented patient model 200 described next below.

A. Resistive Network Model of Biological Patient

Multivariate Z measurement module 120 implements a resistive network model 200 of a patient, as noted above. Resistive network patient model 200 is a lumped element model. The model includes resistive elements each representing the impedance of the different paths traveled by current delivered by electrotherapy device 100. These resistive elements are connected to each other through nodes and the current paths terminate at electrodes 122.

Patient model 200 includes three electrodes 122A–122C and nine (9) resistive elements. The three electrodes 122A–122C are labeled with capital letters A, B and C. The point at which the applied current is delivered into the patient's body is represented by a node of circuit model 200. The nodes are numbered 1, 2 and 3 corresponding to the current delivered by electrodes A, B and C, respectively. That is, the current delivered by electrode A enters the patient's body at node 1; the current delivered by electrode B enters the patient's body at node 2; and the current delivered by electrode C enters the patient's body at node 3. A node 0 is a node through which an applied current passes as it travels from one electrode 122 to another electrode 122, and represents the geometric center of the patient model. Electrodes 122 are placed on the patient's body at approximate predetermined locations such that node 0 is coextensive with the natural heart. For example, in this three electrode scenario, an electrode is placed on the upper right chest, lower left rib cage and the middle back regions of the patient. Other positions are equally effective.

The current delivered by an electrode A–C is subject to an impedance associated with the interface between the electrode and the patient, often referred to as electrode/skin impedance. Such an impedance is caused by the gel used to apply the electrode, skin type, age, perspiration and other well known contributors. In the illustrative embodiment, this impedance is represented by $R_N$ with N being the designated electrode letter, A, B or C. That is, the electrode/skin impedance between terminal node A (electrode A) and the patient (node 1) is $R_A$, the electrode/skin impedance between terminal node B (electrode B) and the patient (node 1) is $R_B$, the electrode/skin impedance between terminal node C (electrode C) and the patient (node 1) is $R_C$. Similarly, the current delivered by each electrode is referred to as $I_N$, with N being the designated electrode. That is, the current delivered by electrode A across impedance $R_A$ is $I_A$, the current delivered by electrode B across impedance $R_B$ is $I_B$, and the current delivered by electrode C across impedance $R_C$ is $I_C$.

Once the current has entered the patient's body, it may either travel toward the geometric center of the patient model (node 0) or it may travel through skeletal muscle tissue (or other conductive tissue) near the surface of the patient to another electrode. The impedance of the organs, tissues, etc., along the expected current path to the node 0 is represented by a resistor $R_{N0}$, where N is the node from which the current travels. Thus, the impedance of the patient's body from node 1 to node 0 is represented by the resistor $R_{10}$. The impedance of the patient's body from node 2 to node 0 is represented by the resistor $R_{20}$. The impedance of the patient's body from node 3 to node 0 is represented by the impedance $R_{30}$ Similarly, the current from each node to node 0 is referred to as $I_{N0}$, with N representing the node number. That is, the current traveling from node 1 to node 0 through resistance $R_{10}$ is $I_{10}$. Similarly, the current traveling from node 2 to node 0 through resistance $R_{20}$ is $I_{20}$, and the current traveling from node 3 to node 0 through resistance $R_{30}$ is $I_{30}$.

Figure 3:
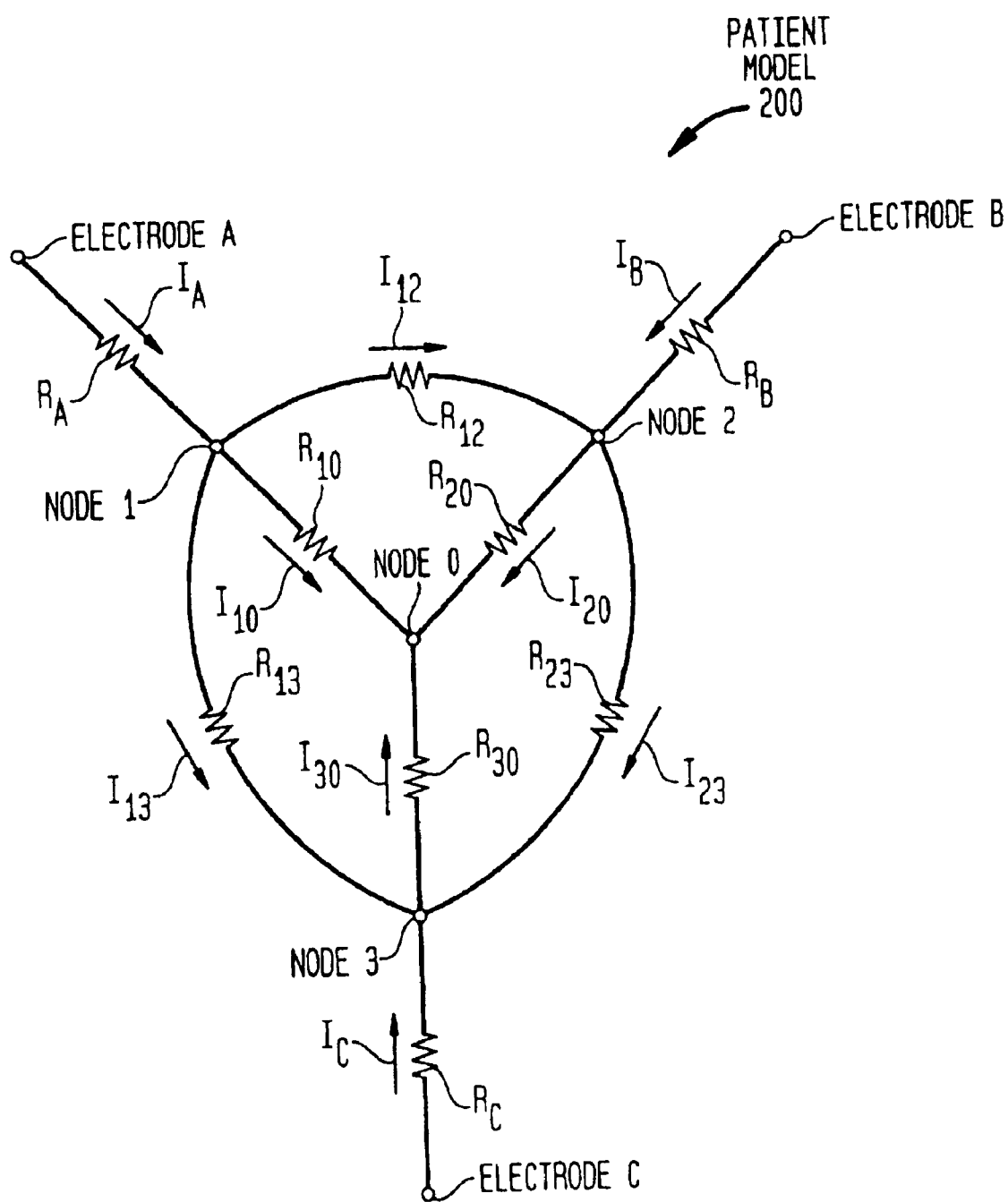
FIG. 3 is a schematic diagram of a resistive network model of a biological patient in accordance with one embodiment of the present invention.

As noted, the current delivered to a patient at one location may also travel across the surface tissue to another electrode rather than through the patient to node 0. The surface through which the current may travel includes any combination of skin, fat, bone and upper layers of muscle, etc. In FIG. 3, the impedance of this current path is referred to as $R_{NM}$, with N representing the source node 1, 2 or 3 while M represents the destination node 1, 2 or 3. Thus, the impedance of the patient's body from node 1 to node 2 is represented by the resistor $R_{12}$. The impedance of the patient's body from node 2 to node 3 is represented by the resistor $R_{23}$. The impedance of the patient's body from node 3 to node 1 is represented by the impedance $R_{31}$. Similarly, the current between these nodes is referred to as $I_{NM}$, with N representing the source node 1, 2 or 3 while M represents the destination node 1, 2 or 3. That is, the current traveling from node 1 to node 2 through resistance $R_{12}$ is $I_{12}$, the current traveling from node 2 to node 3 through resistance $R_{23}$ is $I_{23}$, and the current traveling from node 3 to node 1 through resistance $R_{31}$ is $I_{31}$.

B. Generating the Patient Model Equations

In accordance with the present invention, a series of voltage equations are generated for patient model 200 in terms of the applied currents ($I_A$, $I_B$, $I_C$), measured voltages ($V_A$, $V_B$, $V_C$) and unknown impedance values. Then, during operation, the same network configurations are implemented, the alternating currents are applied and the voltages are measured. The values are inserted into the model equations and the equations are solved for the unknown impedance values. The generation of the patient model equations are described next below, followed by the application of the patient model to a biological patient to determine the impedance values in the model.

As noted above and shown in FIG. 3, patient model 200 includes three electrodes 122A–122C and nine (9) resistive elements. To determine the nine unknown impedance values, nine of the noted voltage and current equations (with the nine unknown impedance terms) are generated. In one embodiment in which the patient model illustrated in FIG. 3 is implemented, the nine equations are generated with the following configuration.

An alternating current is applied across each pair of electrodes (A-B, A-C and B-C) while the voltage is measured across the other electrode pair combinations. In the three electrode embodiment illustrated in FIG. 3, for example, an alternating current source is applied between electrodes A and B while the alternating voltage is measured between electrode pairs A-C, B-C and A-B. For each such configuration, two equations are generated for a total of 6 equations. Then electrodes A and B are shorted together and an alternating current is applied across the shorted electrode and the third electrode; that is, A/B and C. This is repeated for electrode pairs B/C and A and electrodes A/C and B. For each such configuration, one additional equation is generated for a total of 3 equations. In sum, 9 equations are generated.

The generation of three equations for a particular electrode pair (A-B) is provided below. It should be apparent to those of ordinary skill in the art that the same or similar technique can be used to generated the remaining six equations implemented in this 3 electrode, nine resistive element patient model 200.

With a current source $I_S$ applied across electrodes A and B, the applied current travels from the current source through electrode A into the patient, and returns through electrode B. The relationship between the currents relative to $I_S$ are provided in equation (1):

$$I_A = -I_B = I_S \qquad \text{Equation (1)}$$

where, $I_A$=current across electrode-to-skin impedance of electrode A ($R_A$);

$I_B$=current across electrode-to-skin impedance of electrode B ($R_B$); and $I_S$=current applied across electrodes A and B.

Since the current is applied across electrodes A and B, there is no current flowing through electrode C, yielding Equation (2):

$$I_C = 0 \qquad \text{Equation (2)}$$

where, $I_C$=current across electrode-to-skin impedance of electrode C ($R_C$).

Since there is no voltage drop across $R_C$, it follows that the voltage provided by electrode C is the same as the voltage at the node representing the location at which the applied current enters the patient's body, or, $$V_3 = V_C \qquad \text{Equation (3)}$$

where, $V_3$=voltage at node 3; and $V_C$=voltage at electrode C.

The voltage at nodes 1 and 2 are expressed in terms of the electrode voltages in equations 4 and 5:

$$V_1 = V_A - I_A \cdot R_A \qquad \text{Equation (4)}$$
$$= V_A - I_S \cdot R_A$$

where, $V_1$=voltage at node 1;

$V_A$=voltage at electrode A;

$I_A$=current across electrode-to-skin impedance of electrode A;

$I_S$=current applied across electrode-to-skin impedance of electrode A; and $R_A$=electrode-to-skin impedance of electrode A.

$$V_2 = V_B - (I_B \cdot R_B) \qquad \text{Equation (5)}$$
$$= V_B + I_S \cdot R_B$$

where, $V_2$=voltage at node 2;

$V_B$=voltage at electrode B;

$I_B$=current across electrode-to-skin impedance of electrode B;

$I_S$=current applied across electrode-to-skin impedance of electrode B; and $R_B$=electrode-to-skin impedance of electrode B.

The surface currents $I_{13}$, $I_{23}$ and $I_{12}$ can be expressed in terms of the voltages of the nodes 1, 2, and 3 as set forth below in Equations 6, 7 and 8, respectively. Also shown in each equation is the substitution of the electrode voltage values ($V_A$, $V_B$ and $V_C$) for the node values ($V_1$, $V_2$ and $V_3$) since the electrode voltage values are either known or measured.

$$I_{13} = \frac{V_1 - V_3}{R_{13}} = \frac{(V_A - V_C) - I_S \cdot R_A}{R_{13}} \quad \text{Equation (6)}$$

where, $I_{13}$=current traveling near the surface of the patient from node 1 to node 3;
$V_1$=voltage at node 1;
$V_3$=voltage at node 3;
$R_{13}$=patient surface impedance between nodes 1 and 3;
$V_A$=voltage at electrode A;
$V_C$=voltage at electrode C;
$I_S$=current applied across electrode-to-skin impedance of electrode A; and
$R_A$=electrode-to-skin impedance of electrode A.

$$I_{23} = \frac{V_2 - V_3}{R_{23}} = \frac{(V_B - V_C) - I_S \cdot R_B}{R_{23}} \quad \text{Equation (7)}$$

where, $I_{23}$=current traveling near the surface of the patient from node 2 to node 3;
$V_2$=voltage at node 2;
$V_3$=voltage at node 3;
$R_{23}$=patient surface impedance between nodes 2 and 3;
$V_B$=voltage at electrode B;
$V_C$=voltage at electrode C;
$I_S$=current applied across electrode-to-skin impedance of electrode B; and
$R_B$=electrode-to-skin impedance of electrode B $$I_{12} = \frac{V_1 - V_2}{R_{12}} = \frac{(V_A - V_B) - I_S(R_A + R_B)}{R_{12}} \quad \text{Equation (8)}$$

where, $I_{12}$=current traveling near the surface of the patient from node 1 to node 2;
$V_1$=voltage at node 1;
$V_2$=voltage at node 2;
$R_{12}$=patient surface impedance between nodes 1 and 2;
$V_A$=voltage at electrode A;
$V_C$=voltage at electrode C;
$I_S$=current applied across electrode-to-skin impedance of electrodes A & B;
$R_A$=electrode-to-skin impedance of electrode A; and
$R_B$=electrode-to-skin impedance of electrode B.

Kirchhoff's current law dictates that the sum of the currents entering a given node must equal the sum of the currents leaving that node. Applying Kirchhoff's law to each of the three nodes 1, 2 and 3, and rewriting the expressions by substituting into the equations the voltage-current relationship of the individual components, yields Equations 9, 10 and 11. Since this is a resistive circuit model, these resulting equations are algebraic in form.

For node 1, $$I_{10} = I_A - I_{13} - I_{12} \quad \text{Equation (9)}$$

$$= I_S - \frac{(V_A - V_C) - I_S \cdot R_A}{R_{13}} - \frac{(V_A - V_B) - I_S(R_A + R_B)}{R_{12}}$$

where, $I_{10}$=current traveling through the patient from the skin surface at which electrode A is located (node 1) to the geometric center (node 0);
$I_S$=current applied across electrode-to-skin impedance of electrode A; $I_{13}$=current traveling across the surface tissue from the skin surface at which electrode A is located (node 1) to the skin surface at which electrode C is located (node 3); and
$I_{12}$=current traveling across the surface tissue from the skin surface at which electrode A is located (node 1) to the skin surface at which electrode B is located (node 2).

For node 2, $$I_{20} = I_B + I_{12} - I_{23} \quad \text{Equation (10)}$$

$$= -I_S - \frac{(V_A - V_B) - I_S(R_A + R_B)}{R_{12}} - \frac{(V_B - V_C) + I_S \cdot R_B}{R_{23}}$$

where, $I_{20}$=current traveling through the patient from the skin surface at which electrode is located (node 2) to the geometric center (node 0);
$I_S$=current applied across electrode-to-skin impedance of electrode B;
$I_{12}$=current traveling near the surface tissue from the skin surface at which electrode A is located (node 1) to the skin surface at which electrode B is located (node 2); and
$I_{23}$=current traveling near the surface tissue from the skin surface at which electrode B is located (node 2) to the skin surface at which electrode C is located (node 3).

For node 3, $$I_{30} = I_{13} + I_{23} \quad \text{Equation (11)}$$

$$= \frac{(V_A - V_C) - I_S \cdot R_A}{R_{13}} - \frac{(V_B - V_C) + I_S \cdot R_B}{R_{23}}$$

$$I_{30} = I_{13} + I_{23}$$

$$\frac{(V_A - V_C) - I_S \cdot R_A}{R_{13}} - \frac{(V_B - V_C) + I_S \cdot R_B}{R_{23}}$$

where, $I_{30}$=current traveling through the patient from the skin surface at which electrode C is located (node 3) to the geometric center (node 0);
$I_{13}$=current traveling near the surface tissue from the skin surface at which electrode A is located (node 1) to the skin surface at which electrode C is located (node 3); and
$I_{23}$=current traveling near the surface tissue from the skin surface at which electrode B is located (node 2) to the skin surface at which electrode C is located (node 3).

Each of the node voltages can be expressed in terms of the other node voltages since they are all connected through an internal impedance to node 0 at the geometric center. At node 0, the voltage $V_0$ can be expressed in terms relative to each node 1, 2 and 3.

$$V_0 = V_1 - I_{10} \cdot R_{10} = V_3 - I_{30} \cdot R_{30} = V_2 - I_{20} \cdot R_{20} \qquad \text{Equation (12)}$$

where, $R_{10}$=impedance of path through patient from the skin surface at which electrode A is located (node 1) and geometric center (node 0);

$R_{20}$=impedance of path through patient from the skin surface at which electrode B is located (node 2) and geometric center (node 0); and $R_{30}$=impedance of path through patient from the skin surface at which electrode C is located (node 3) and geometric center (node 0).

The portion of Equation 12 that expresses the relationship between nodes 1 and 3 can be rewritten as shown in Equation 13 below when the values derived above are substituted.

$$V_1 - I_{10} * R_{10} = V_3 - I_{30} * R_{30} \qquad \text{Equation (13)}$$

$$(V_A - I_S * R_A) - \left[I_S - \frac{(V_A - V_C) - I_S * R_A}{R_{13}} - \frac{(V_A - V_B) - I_S(R_A + R_B)}{R_{12}}\right] R_{10} =$$

$$V_C - \left[\frac{(V_A - V_C) - I_S * R_A}{R_{13}} + \frac{(V_B - V_C) + I_S * R_B}{R_{23}}\right] R_{30}$$

Similarly, the portion of Equation 12 that expresses the relationship between nodes 2 and 3 can be written as shown in Equation 14 when the values defined above are substituted into Equation 11.

$$V_2 - I_{20} \cdot R_{20} = V_3 - I_{30} \cdot R_{30} \qquad \text{Equation (14)}$$

$$(V_B - I_S \cdot R_B) - \left[-I_S - \frac{(V_A - V_B) - I_S(R_A + R_B)}{R_{12}} - \frac{(V_B - V_C) - I_S \cdot R_B}{R_{23}}\right] R_{20} =$$

$$V_C - \left[\frac{(V_A - V_C) - I_S \cdot R_A}{R_{13}} + \frac{(V_B - V_C) + I_S \cdot R_B}{R_{23}}\right] R_{30}$$

In Equations 13 and 14, all of the voltage and current values are known quantities, and each equation is expressed in terms of unknown resistance values. Thus, these are two equations derived from the application of current source $I_S$ between electrodes A and B while measuring the alternating voltage between electrode pair A-C and electrode pair B-C. Similarly, two additional equations can be derived by measuring the alternating voltage between electrode pairs B-A and C-A while current source $I_S$ is applied between electrode pair B-C, and two more equations can be derived by measuring the alternating voltage between electrode pairs A-B and C-B while current source $I_S$ is applied between electrode pair A-C. As noted, this yields a total of six equations with nine unknown resistance values.

To derive the remaining three equations required to determine the nine unknown resistance values, certain nodes are combined as described below. In accordance with one embodiment of the invention, two nodes are shorted together and the current source $I_S$ is applied between the shorted nodes and the remaining third node. The resistance at each node is the parallel combination of all resistive elements connected to that node. These resistance values are set forth below in Equations 15–18.

$$R_0 = \frac{1}{\frac{1}{R_{10}} + \frac{1}{R_{20}} + \frac{1}{R_{30}}} \qquad \text{Equation (15)}$$

$$R_1 = \frac{1}{\frac{1}{R_A} + \frac{1}{R_{13}} + \frac{1}{R_{12}} + \frac{1}{R_{10}}} \qquad \text{Equation (16)}$$

$$R_2 = \frac{1}{\frac{1}{R_B} + \frac{1}{R_{12}} + \frac{1}{R_{20}} + \frac{1}{R_{23}}} \qquad \text{Equation (17)}$$

$$R_3 = \frac{1}{\frac{1}{R_C} + \frac{1}{R_{13}} + \frac{1}{R_{23}} + \frac{1}{R_{30}}} \qquad \text{Equation (18)}$$

The voltage and current terms at each electrode under the noted condition in which electrodes A and B are shorted together and the current source $I_S$ is applied between the shorted nodes A/B and the remaining third node C is expressed in Equation (19):

$$V_A = V_B$$

$$V_C = 0$$

$$I_S = I_A + I_B = -I_C \qquad \text{Equation (19)}$$

Applying Kirchhoff's law to nodes 0–3 of patient model 200 under this condition results in Equations 20–23 as set forth below. In each case, the equation is also shown rewritten with the voltage $V_0$, $V_1$, $V_2$, and $V_3$ and impedance values substituted for the current terms, followed by a further substitution with the resistance values as defined in Equations 15–19 above. This results in an equation in terms of the unknown resistance values and the voltages at nodes 0–3.

For node 0:

$$I_{10} + I_{20} + I_{30} = 0 \qquad \text{Equation (20)}$$

$$\frac{V_1 - V_0}{R_{10}} + \frac{V_2 - V_0}{R_{20}} + \frac{V_3 - V_0}{R_{30}} = 0$$

$$\left(\frac{1}{R_{10}} + \frac{1}{R_{20}} + \frac{1}{R_{30}}\right) V_0 + \frac{1}{R_{10}} V_1 + \frac{1}{R_{20}} V_2 + \frac{1}{R_{30}} V_3 = 0$$

$$\frac{1}{R_0} V_0 + \frac{1}{R_{10}} V_1 + \frac{1}{R_{20}} V_2 + \frac{1}{R_{30}} V_3 = 0$$

For node 1:

$$I_A - I_{13} - I_{10} - I_{12} = 0 \qquad \text{Equation (21)}$$

$$\frac{V_A - V_1}{R_A} + \frac{V_3 - V_1}{R_{13}} + \frac{V_0 - V_1}{R_{10}} + \frac{V_2 - V_1}{R_{12}} = 0$$

$$\frac{1}{R_{10}} V_0 - \frac{1}{R_1} V_1 + \frac{1}{R_{12}} V_2 + \frac{1}{R_{13}} V_3 = -\frac{V_A}{R_A}$$

For node 2:

$$I_B - I_{20} - I_{23} + I_{12} = 0 \quad \text{Equation (22)}$$

$$\frac{V_0 - V_2}{R_B} + \frac{V_1 - V_2}{R_{12}} + \frac{V_0 - V_2}{R_{20}} + \frac{V_3 - V_2}{R_{23}} = 0$$

$$\frac{1}{R_{20}}V_0 + \frac{1}{R_{12}}V_1 - \frac{1}{R_2}V_2 + \frac{1}{R_{23}}V_3 = -\frac{V_B}{R_B}$$

For node 3:

$$I_C - I_{30} - I_{13} + I_{23} = 0 \quad \text{Equation (23)}$$

$$\frac{0 - V_3}{R_C} + \frac{V_0 - V_3}{R_{30}} + \frac{V_1 - V_3}{R_{13}} + \frac{V_2 - V_3}{R_{23}} = 0$$

$$\frac{1}{R_{30}}V_0 - \frac{1}{R_{13}}V_1 + \frac{1}{R_{23}}V_2 - \frac{1}{R_{30}}V_3 = 0$$

Placing Equations 20–23 in matrix form yields Equation 24:

$$\begin{bmatrix} -\frac{1}{R_0} & \frac{1}{R_{10}} & \frac{1}{R_{20}} & \frac{1}{R_{30}} \\ \frac{1}{R_{10}} & -\frac{1}{R_1} & \frac{1}{R_{12}} & \frac{1}{R_{13}} \\ \frac{1}{R_{20}} & \frac{1}{R_{12}} & -\frac{1}{R_2} & \frac{1}{R_{23}} \\ \frac{1}{R_{30}} & \frac{1}{R_{13}} & \frac{1}{R_{23}} & -\frac{1}{R_3} \end{bmatrix} \begin{bmatrix} V_0 \\ V_1 \\ V_2 \\ V_3 \end{bmatrix} = \begin{bmatrix} 0 \\ -\frac{V_A}{R_A} \\ -\frac{V_B}{R_B} \\ 0 \end{bmatrix} \quad \text{Equation (24)}$$

↑

Matrix A

Equations 20–23 (and the matrix form shown in Equation 24) provide four equations with four unknown voltages, $V_0$, $V_1$, $V_2$ and $V_3$. Applying Kramer's Rule to solve for $V_3$ yields the matrix illustrated in Equation 25 below.

$$\begin{bmatrix} -\frac{1}{R_0} & \frac{1}{R_{10}} & \frac{1}{R_{20}} & 0 \\ \frac{1}{R_{10}} & -\frac{1}{R_1} & \frac{1}{R_{12}} & -\frac{V_A}{R_A} \\ \frac{1}{R_{20}} & \frac{1}{R_{12}} & -\frac{1}{R_2} & -\frac{V_B}{R_B} \\ \frac{1}{R_{30}} & \frac{1}{R_{13}} & \frac{1}{R_{23}} & 0 \end{bmatrix} = \text{Matrix } A_3 \quad \text{Equation (25)}$$

$V_3$ is then determined by calculating the determinant of matrix $A_3$ divided by the determinant of matrix A, as shown in Equation 26.

$$V_3 = \frac{\det(A_3)}{\det(A)} = R_C \cdot I_S \quad \text{Equation (26)}$$

As shown by the above derivation, the expressions resulting from the operations shown in Equation 26 will be of a form in which all of the voltage and current values are known quantities, and the equation is expressed in terms of unknown resistance values. Thus, for this second configuration in which nodes A and B are shorted together and the alternating current is applied across the shorted notes A/B and node C results in the generation of the third equation, Equation 26. This process is to be repeated for the remaining electrode pair combinations A-C and B-C, each resulting in the generation of an additional equation, for a total of nine equations.

It should be understood that patient model 200 is provided for exemplary purposes only and that other patient models are possible. For example, in applications in which the applied current can take an additional path through the biological patient, additional resistive terms could be added to the patient model. In other embodiments, more than three electrodes can be implemented, as noted above.

Returning to FIG. 2, multivariate Z measurement module 120 includes, as noted a multi-electrode pair control circuit 204. This circuit 204 is connected to a DC current source 212 from which it receives a DC source current 214. This current is converted to an alternating source current $I_{S-AC}$ 216. The alternating source current 216 has a frequency determined by controller 202 through the generation of frequency control signals 206. Alternating source current 216 is applied to selected electrode pairs based on an electrode selection signal 208 also generated by controller 202. Electrode selection signals 208 also determine which electrode pairs across which a voltage measurement is taken. The results of such measurements are provided to controller 202 as shown by voltage signals 210. The details of multivariate Z measurement module 120 are described next below.

III. Multivariate Z Measurement Module

Figure 4:
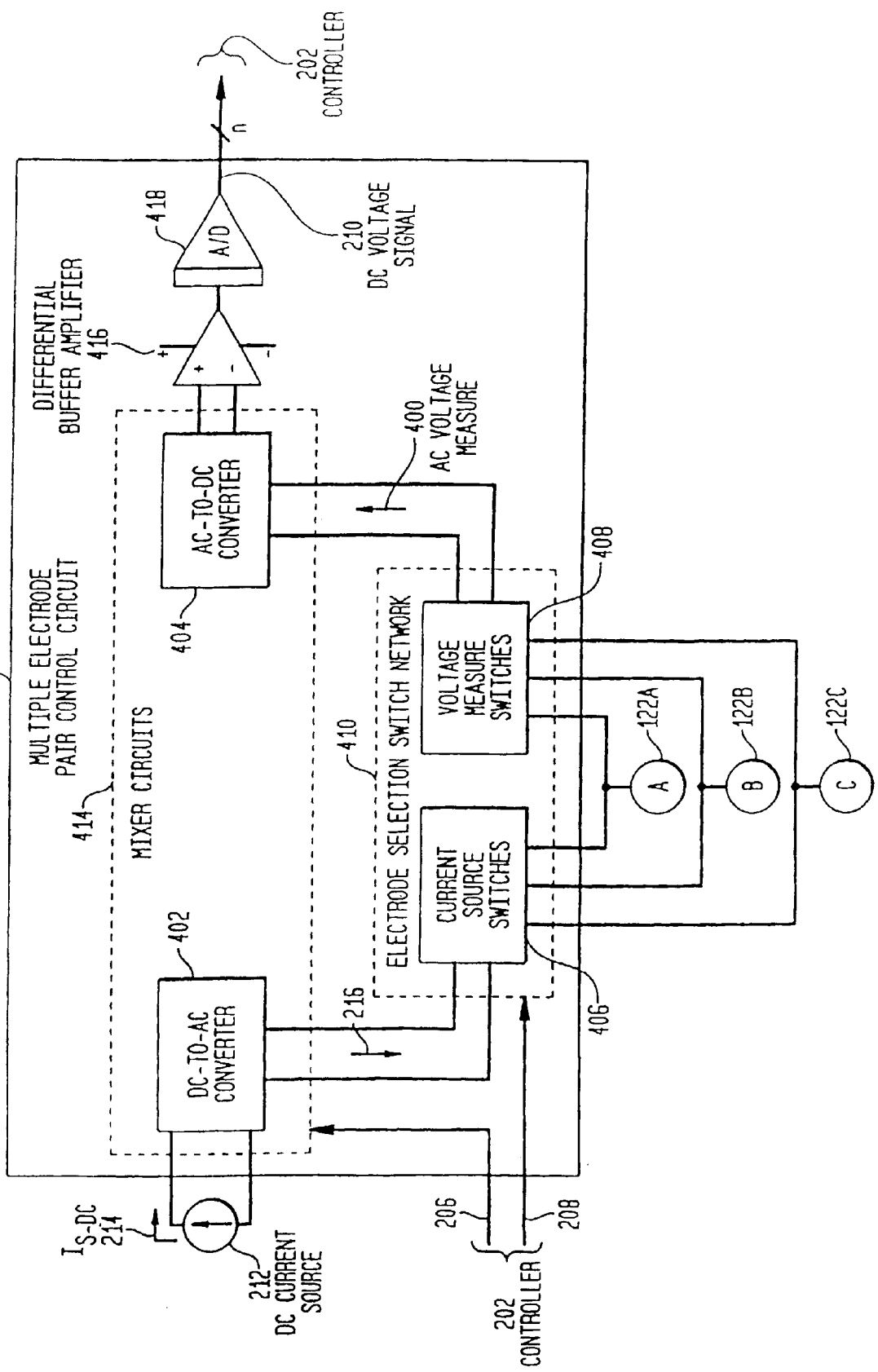
FIG. 4 is a functional block diagram of the multivariate impedance measurement module in accordance with one embodiment of the present invention.
Figure 5:
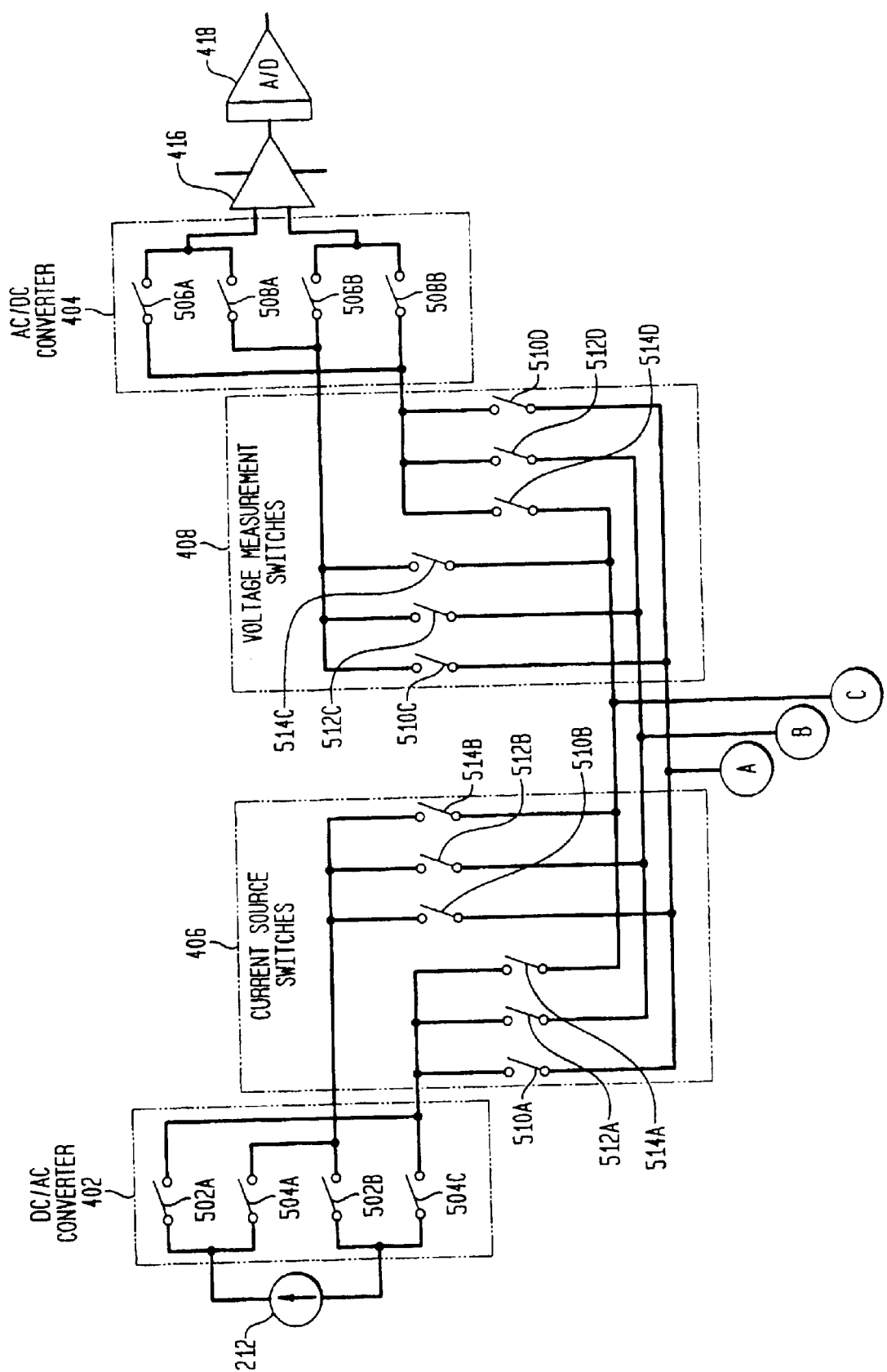
FIG. 5 is a detailed schematic diagram of the multivariate impedance measurement module in accordance with one embodiment of the present invention.

FIG. 4 is a more detailed block diagram of multi-electrode pair control circuit 204. FIG. 5 is a simplified schematic diagram of one implementation of the primary components illustrated in FIG. 4. Referring first to FIG. 4, multiple electrode pair control circuit 204 includes mixer circuits 414 and an electrode selection switch network 410. Mixer circuits 414 include a DC-to-AC converter circuit 402 and an AC-to-DC converter circuit 404, and is controlled by controller 202 to synchronously convert DC current 214 to AC current 216 and AC voltage measurement signals 401 to a DC voltage signal 210. Specifically, DC-to-AC converter circuit 402 is implemented as a frequency multiplexer that converts DC current 214 to AC current 216. Similarly, AC-to-DC converter circuit 404 is implemented as a frequency demultiplexer, converting AC voltage measurements 401 to DC voltage signal 210.

DC voltage signal 210 is passed through a differential buffer amplifier and an A/D converter 418. Mixer circuits 414 are operated at a frequency consistent with the implemented A/D converter 418. For example, in certain embodiments, A/D converter 418 may also be used in electrotherapy device 100 to measure ECG signals. In such embodiments, the frequency of AC-to-DC converter 404 may be in the order of 32 kHz to accommodate the implemented A/D converter. In alternative embodiments, mixer circuits 414 are operated at other frequencies. It should be understood that mixer circuits 414 need not include AC-to-DC converter 404 in alternative embodiments, such as when an A/D converter 418 suitable to directly convert AC voltage signal 401 is implemented. Such multiplexers and demultiplexers are considered to be well known in the art and, therefore, are not described further herein.

Multiple electrode pair control circuit 204 also includes an electrode selection switch network 410 that, as noted, makes the necessary electrical connections to implement the application of AC current 216 to a selected pair of electrodes 122. Further, selection switch network 410 makes the necessary electrical connections to implement the measurement of voltage across a selected pair of electrodes 122. As shown in the embodiment of switch network 410 illustrated in FIG. 4, there are functionally two sets of switch networks, current source switches 406 for controlling the application of current 216 and a voltage measurement switch network 408 that controls the voltage measurements. Electrode selection switch network 410 is responsive to selection signals 208 generated by controller 202 as described further below.

Referring now to FIG. 5, DC-to-AC converter 402 is implemented as a frequency multiplexer with four switches 502A, 502B, 504A and 504B. Similarly, AC-to-DC converter 404 is implemented as a frequency demultiplexer with four switches 506A, 506B, 508A and 508B. Converters 402 and 404 together form mixing circuits 414 as noted above, and are responsive to frequency control signals 306 generated by controller 202. For ease of illustration, the signal lines that carry frequency control signals 206 have been omitted from FIG. 5.

Switches 502 and 504 are connected to each electrode 122 independently of each other through current source switches 406. For each cycle of the implemented frequency, switches 502A and 502B are switched on and switches 504A and 504B are switched off for the positive half cycle of the desired frequency. Similarly, switches 504A and 504B are switched on and switches 502A and 502B are switched off for the negative half cycle of the desired frequency.

Frequency demultiplexer 404 operates in a similar fashion. That is, switches 506A and 506B are switched together while switches 508A and 508B are switched together. The phase relationship between the frequency of frequency multiplexer 402 and frequency demultiplexer 404 determines whether the real (resistance) or imaginary (reactance) part of the impedance is measured. To measure resistance, for example, switches 506 are switched with switches 502 and switches 508 are switched with switches 504. On the other hand, to measure impedance, switches 506 are switched with a 90 degree phase shift from switches 502 and switches 508 are switched with a 90 degree phase shift from switches 504.

Current source switch network 406 connects the alternating current provided by frequency multiplexer 402 to selected electrode pairs. Switch network 406 includes six switches. Three switches 510A, 512A and 514A selectively connect one side of the current source from DC-to-AC converter 402 to electrodes 122A, 122B and 122C, respectively, while three switches 510B, 512B and 514B selectively connect the other side of the current source from DC-to-AC converter 402 to electrodes 122A, 122B and 122C, respectively.

Current source switch network 406 connects the alternating current provided by DC-to-AC converter 402 to selected electrode pairs. For example, to connect the output of DC-to-AC converter 402 to electrode pair A-B, switches 510A and 512B are closed and the other switches of switch network 406 are opened. To connect the output of DC-to-AC converter 402 to electrode pair B-C, switches 512A and 514B are closed and the other switches of switch network 406 are opened. To connect the output of DC-to-AC converter 402 to electrode pair A-C, switches 510A and 51 4B are closed and the other switches of switch network 406 are opened.

Voltage measurement switch network 408 is controlled in a similar manner. Voltage measurement switch network 408 connects the measured alternating voltage 401 provided by electrodes 122 to selected input lines to AC-to-DC converter 404. Switch network 408 includes six switches. Three switches 510C, 512C and 514C selectively connect one voltage sense line from electrodes 122A, 122B and 122C to AC-to-DC converter 404, respectively, while three switches 510D, 512D and 514D selectively connect the other voltage sense line from electrodes 122A, 122B and 122C to AC-to-DC converter 404, respectively.

Voltage measurement switch network 408 connects the alternating voltage 401 provided by selected pairs of electrodes 122 to frequency demultiplexer 404. For example, to connect electrode pair A-B to AC-to-DC converter 404, switches 510C and 512D are closed and the other switches of switch network 408 are opened. To connect electrode pair B-C to AC-to-DC converter 404, switches 512C and 514D are closed and the other switches of switch network 408 are opened. To connect electrode pair A-C to AC-to-DC converter 404, switches 510C and 514D are closed and the other switches of switch network 408 are opened.

It should be understood that switches 502-514 can be implemented in any well-known manner. For example, in one embodiment, switches 502-504 are implemented in an integrated circuit. In such embodiments, controller 202 can be implemented as part of controller 106 (FIG. 1). Other implementations may be implemented depending on the application.

III. Closing

It should be understood that various changes and modifications of the embodiments shown in the drawings and described in the specification may be made within the spirit and scope of the present invention. Accordingly, it is intended that all matter contained in the above description and shown in the accompanying drawings be interpreted in an illustrative and not in a limiting sense. The invention is limited only as defined in the following claims and the equivalents thereto.

What is claimed is:

1. A multivariate impedance measurement module, for use in an electrotherapy device, said module comprising:

a multiple electrode pair control circuit adapted to provide an alternating current, said control circuit connected to at least three electrodes, the electrodes external to the control circuit and adapted to be placed at predetermined relative locations on a patient's body;

a controller for controlling said multiple electrode pair control circuit to
  (a) successively apply the alternating current to all possible pairs of the at least three electrodes, and, during each such application of alternating current, successively measure a voltage across all remaining electrode pairs other than the electrode pair to which the current is being applied; and
  (b) short each combination of two of the at least three electrodes and apply the alternating current and measure a voltage across each combination of shorted electrodes and the remaining non-shorted electrode, wherein said controller further comprises a resistive network model of the patient's body, said model defined by voltage/current equations having terms representing an impedance of each current path between the at least three electrodes through the patient, wherein the controller solves the equations for the terms representing the impedance of each current path between the at least three electrodes with information obtained by said controller in (a) and (b).

2. The multivariate impedance measurement module of claim 1, wherein said measurement module is adapted for the electrotherapy device selected from the group consisting of a cardioverter, a defibrillator and a pacemaker.

3. The multivariate impedance measurement module of claim 1, wherein said resistive network model includes resistive elements each representing an impedance of a current path that connects nodes of the network model, said nodes respectively comprising a point at which alternating current delivered by each of said at least three electrodes enters the patient's body.

4. The multivariate impedance measurement module of claim 3, wherein said resistive elements comprise:

a plurality of resistive elements each representing an electrode/skin impedance between each of said at least three electrodes and a corresponding location at which current delivered by each said electrode is adapted to be delivered into the patient's body.

5. The multivariate impedance measurement module of claim 4, wherein said resistive elements further comprise:

an impedance of each current path from the corresponding location at which current is delivered into the patient's body and a geometric center of said resistive network model.

6. The multivariate impedance measurement module of claim 5, wherein said resistive elements further comprise:

an impedance of a current path from a first location at which current is delivered into the patient's body to a second location at which current exits the patient's body.

7. The multivariate impedance measurement module of claim 1, wherein said controller is adapted to solve the voltage/current equations for the impedance of current paths utilizing said applied currents and measured voltages.

8. The multivariate impedance measurement module of claim 7, wherein said multiple electrode pair control circuit further comprises:

an electrode selection switch network configured to apply the alternating current to successive electrode pairs, and to measure a voltage across each electrode pair other than a selected electrode pair.

9. The multivariate impedance measurement module of claim 7, wherein said multiple electrode pair control circuit further comprises:

a DC-to-AC converter for converting DC current from an external DC current source to alternating current having a first frequency.

10. The multivariate impedance measurement module of claim 9, wherein said multiple electrode pair control circuit further comprises:

an AC-to-DC converter for converting an AC voltage signal across an electrode pair to a DC voltage signal.

* * * * *